United States Patent [19]

Brennan et al.

[11] 4,191,693
[45] Mar. 4, 1980

[54] PREPARATION OF GAMMA-PYRONES FROM 3-SUBSTITUTED FURANS

[75] Inventors: Thomas M. Brennan, Old Lyme; Daniel P. Brannegan, Pawcatuck; Paul D. Weeks; Donald E. Kuhla, both of Gales Ferry, all of Conn.

[73] Assignee: Pfizer, Inc., New York, N.Y.

[21] Appl. No.: 937,408

[22] Filed: Aug. 28, 1978

Related U.S. Application Data

[62] Division of Ser. No. 741,348, Nov. 12, 1976, Pat. No. 4,126,624.

[51] Int. Cl.$^2$ .............................................. C07D 309/22
[52] U.S. Cl. ................................................ 260/345.9 R
[58] Field of Search ................................... 260/345.9 R

[56] References Cited

U.S. PATENT DOCUMENTS

| | | | |
|---|---|---|---|
| 3,751,434 | 8/1973 | Lefebvre | 260/345.9 R |
| 4,059,595 | 11/1977 | Shono et al. | 260/345.9 R |
| 4,082,717 | 4/1978 | Brennan et al. | 260/345.9 R |

OTHER PUBLICATIONS

Shono et al., Tetrahedron Letters, 17, 1363 (1976).
Laliberte et al., J. Med. Chem., 16, 1084 (1973).
Achmatowice, Jr. et al., Tetrahedron, 32, 1051 (1976).
Achmatowicz, Jr. et al. Tetrahedron, 27, 1973 (1971).
Torii et al., Chemistry Letters, 5, 495 (1976).

Primary Examiner—Nicky Chan
Attorney, Agent, or Firm—Connolly and Hutz

[57] ABSTRACT

Gamma-pyrones are prepared by contacting a 3-halo-furfuryl alcohol or a 3-alkoxy-furfuryl alcohol with one equivalent of a halogen, peracid or peroxide oxidant and then heating until hydrolysis of the formed 4-substituted-dihydropyran intermediate is substantially complete. Maltol (2-methyl-3-hydroxy-4H-pyran-4-one) is prepared by this process from 2(1-hydroxyethyl)-3-alkoxy furans or 2(1-hydroxyethyl)-3-halo-furans. Gamma-pyrones are also prepared by contacting the corresponding 3-substituted-2,5-dialkoxy-furfuryl alcohols with acid until conversion to the gamma-pyrones is substantially complete.

10 Claims, No Drawings

PREPARATION OF GAMMA-PYRONES FROM 3-SUBSTITUTED FURANS

CROSS REFERENCE TO RELATED APPLICATION

This application is a division of application Ser. No. 741,348 filed Nov. 12, 1976, now U.S. Pat. No. 4,126,624.

BACKGROUND OF THE INVENTION

Maltol is a naturally occurring substance found in the bark of young larch trees, pine needles and chicory. Early commercial production was from the destructive distillation of wood. Synthesis of maltol from 3-hydroxy-2-(1 piperidylmethyl)-1,4-pyrone was reported by Spielman and Freifelder in J. Am. Chem. Soc. 69, 2908 (1947). Schenck and Spielman, J. Am. Chem. Soc. 67, 2276 (1945), obtained maltol by alkaline hydrolysis of streptomycin salts. Chawla and McGonigal, J. Org. Chem. 39, 3281 (1974), and Lichtenthaler and Heidel, Angew. Chem. 81, 999 (1969), reported the synthesis of maltol from protected carbohydrate derivatives. Synthesis of gamma-pyrones, such as pyromeconic acid, maltol, ethyl maltol and other 2-substituted-3-hydroxy-gamma-pyrones are described in U.S. Pat. Nos. 3,130,204; 3,133,089; 3,140,239; 3,159,652; 3,365,469; 3,376,317; 3,468,915; 3,440,183 and 3,446,629.

Multi-step syntheses based on furfuryl alcohols and requiring the preparation of intermediate epoxy ketones have been reported by Shono and Matsumura, Tetrahedron Letters No. 17, 1363 (1976), Torii et al., Chemistry Letters, No. 5, 495 (1976) and such a synthesis is described in co-pending U.S. Pat. application Ser. No. 608,452, filed Aug. 28, 1975, assigned to the assignee of the present application. A one-pot process for preparing useful gamma-pyrones from unsubstituted furfuryl alcohols is described in co-pending U.S. Pat. application Ser. No. 710,901, filed Aug. 2, 1976, now abandoned.

Maltol and ethyl maltol enhance the flavor and aroma of a variety of food products. In addition, these materials are used as ingredients in perfumes and essences. The 2-alkenyl-pyromeconic acids reported in U.S. Pat. No. 3,644,635 and the 2-aryl-methylpyromeconic acids described in U.S. Pat. No. 3,365,469 inhibit the growth of bacteria and fungi and are useful as flavor and aroma enhancers in foods and beverages and aroma enhancers in perfumes.

SUMMARY OF THE INVENTION

The present invention relates to the preparation of useful gamma-pyrones such as maltol (2-methyl-3-hydroxy-4H-pyran-4-one) and related compounds. A novel process is provided for the preparation of such compounds which comprises contacting a 3-substituted-furfuryl alcohol of the formula

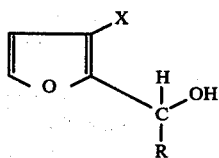

wherein R is hydrogen, alkyl of 1 to 4 carbon atoms, phenyl or benzyl, and X is chloride, bromide, iodide or alkoxyl of 1 to 4 carbon atoms, with at least one equivalent of a halogen, peracid or peroxide oxidant and heating to hydrolyze the intermediate 4-substituted-dihydropyran to the desired gamma-pyrone. The process can be adapted to prepare and isolate the intermediate 4-substituted-6-hydroxy-pyran-3-ones by contacting a 3-substituted-furfuryl alcohol with an oxidant of the type described above at temperatures below about 25° C. such that there is no substantial secondary reaction to the corresponding gamma-pyrone. The isolated 4-substituted-6-hydroxy-pyran-3-ones are readily converted to the corresponding gamma-pyrones by hydrolysis in the presence of an acid.

Gamma-pyrones are also prepared from related compounds of the formula

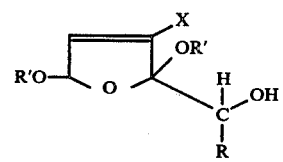

wherein R and X are as described above and R' is an alkyl group of 1 to 4 carbon atoms. Gamma-pyrones are prepared by contacting these compounds with an acid until conversion to the corresponding gamma-pyrone is substantially complete. The intermediate 4-substituted-6-alkoxy-pyran-3-ones can be prepared and isolated by contacting the 3-substituted-2,5-dialkoxyfurfuryl alcohols in non-aqueous solution with an acid at a temperature below about 25° C. such that there is no substantial conversion to the corresponding gamma-pyrone. Gamma-pyrones can be prepared from the isolated 4-substituted-6-alkoxy-pyran-3-ones by hydrolysis in the presence of an acid.

DETAILED DESCRIPTION OF THE INVENTION

The present invention relates to thepreparation of useful gamma-pyrones from 3-substituted furfuryl alcohols. Specifically, 3-halo-furfuryl alcohols and 3-alkoxy-furfuryl alcohols of the formula

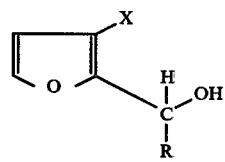

wherein R is hydrogen, alkyl of 1 to 4 carbon atoms, phenyl or benzyl, and X is chloride, bromide, iodide or alkoxyl of 1 to 4 carbon atoms, are readily converted by a one-pot process to useful gamma-pyrones by contacting the appropriate 3-substituted-furfuryl alcohol in aqueous solution with at least one equivalent of an oxidant selected from a halogen, a peracid or a peroxide. The reaction mixture is then heated to hydrolyze the final formed 4-substituted-6-hydroxy-pyran-3-one to the desired gamma-pyrone. The reaction scheme of the one-pot process is:

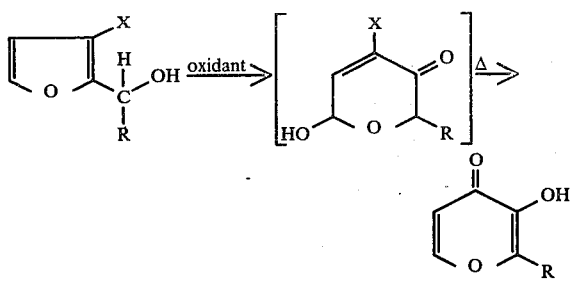

wherein R and X are as described above.

The 3-substituted-furfuryl alcohol starting materials can be prepared by known methods, for example, by reaction of a Grignard reagent with a 3-substituted-furfural, which may be prepared by methods described in the literature. For example, see Bull. Soc. Chim. France, 1971, 990; C. R. Acad. Sci. Paris, Ser. C, 264, 413 (1967), Chem. Abs., 67, 32662s; Nippon Kagaku Zasshi, 79, 1366 (1958), Chem. Abs., 54, 24633 g. 3-substituted-furfuryl alcohols may also be prepared by reacting 3-substituted furans with acid anhydrides, such as acetic or propionic anhydride, to give the 2-acyl-compound followed by reduction of the carbonyl with sodium borohydride.

For the synthesis of maltol, the 3-halo- or 3-alkoxy-substituted-methyl-furfuryl alcohol can be prepared from isomaltol (2-acetyl-3-hydroxy-furan) which is readily derived from lactose. The 3-hydroxy substituent is converted to halo- or alkoxyl by known methods, for example by reaction with $PCl_5$ to give the 3-chloro-compound, and with a dialkyl sulfate in basic solution to give the alkoxyl compounds. The carbonyl group of the 2-acetyl substituent is then reduced to hydroxyl by use of an effective reducing agent such as sodium borohydride.

The preferred oxidants for the present one-pot process are the halogens, by which is meant chlorine, bromine, chlorine-bromine, hypochlorous acid, hypobromous acid and mixtures thereof. Of these, chlorine and chlorine-bromine prepared in situ by the addition of chlorine to a solution of sodium or potassium bromide are preferred for reasons of cost. Other oxidants may, however be used in the present process, particularly peracids such as peracetic acid and m-chloroperbenzoic acid and peroxides such as hydrogen peroxide or t-butyl peroxide. Peracids in organic solvents were used by Lefebvre et al. in J. Med. Chem. 16, 1084 (1973) to oxidize unsubstituted furfuryl alcohols to 6-hydroxy-2H-pyran-3(6H)-ones. In the present process a 4-halo- or 4-alkoxy-6-hydroxy-2H-pyran-3(6H)-one is formed as an intermediate and it has been found that according to the present invention the desired gamma-pyrone is readily obtainable by subsequent hydrolysis of this compound. While the use of a halogen oxidant is critical in the conversion of unsubstituted furfuryl alcohols to gamma-pyrones described in co-pending U.S. Pat. application Ser. No. 710,901, filed Aug. 2, 1976, the presence of the 3-halo- or 3-alkoxy-substituent of the starting furfuryl alcohol makes the use of other oxidants feasible in the present process.

The one-pot process of the present invention is conducted in water or in water with an organic co-solvent. The co-solvent can be water-miscible or water-immiscible and can be selected from a wide range of solvents. Preferred as co-solvents are alkanols and alkanediols of 1 to 4 carbon atoms, dialkyl and cycloalkyl ethers of 2 to 10 carbon atoms and dialkyl ketones of 3 to 10 carbon atoms. Of these types of solvents specifically preferred solvents are methanol, tetrahydrofuran, isopropyl ether and acetone. Other solvents may, however, be used, including lower alkyl esters of 3 to 10 carbon atoms and alkyl nitriles and amides of 2 to 4 carbon atoms.

In the present one-pot process one equivalent of an oxidant selected from a halogen, a peracid or a peroxide, as described above, is slowly added to a solution of the 3-halo- or 3-alkoxy-furfuryl alcohol in water or water and organic co-solvent. Alternatively, the oxidant and the 3-substituted-furfuryl alcohol are added dropwise simultaneously to the water or water-organic solvent. The solvent is well stirred throughout the addition of reactants and the temperature is maintained between about −50° C. and 50° C., preferably between about −10° C. and 10° C. After addition of reactants is complete, low boiling co-solvents, if employed, can optionally be removed by distillation. The solution is then heated to effect hydrolysis of the final formed 4-substituted-6-hydroxy-dihydropyran intermediate. The solution is heated to a temperature at which the rate of the hydrolysis proceeds at a reasonable rate, generally from about 70° C. to 160° C., preferably 90° C. to 110° C. The 3-alkoxy-furfuryl alcohols and the immediates formed therefrom are more reactive than the corresponding 3-halo-compounds and require lower temperatures to effect the final hydrolysis reaction. In fact, temperatures between about 25° C. and 160° C. can be employed for the 3-alkoxyl compounds. The solution is heated until conversion of the intermediate 4-substituted-6-hydroxy-dihydropyran is substantially complete, in general, about 1 to 3 hours. The acid necessary to catalyze this final hydrolysis may be generated in situ in the one-pot process by heating or acid may be added.

If desired, the one-pot process can be adapted to prepare and isolate the 4-halo- or 4-alkoxy-6-hydroxy-pyran-3-one intermediate of the formula

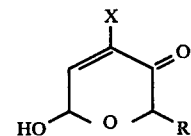

wherein R is hydrogen, alkyl of 1 to 4 carbon atoms, phenyl or benzyl and X is chloride, bromide, iodide or alkoxyl of 1 to 4 carbon atoms, by use of conditions where the final hydrolysis is not effected. Thus, a 3-halo- or 3-alkoxy-furfuryl alcohol is contacted in water, or water-organic co-solvent of the type described above, with at least one equivalent of an oxidant selected from a halogen, a peracid or a peroxide. The temperature should be maintained between about −50° C. and 25° C., preferably −10° C. to 10° C. such that substantially no secondary reaction to the corresponding gamma-pyrone occurs; at these temperatures the rates of the hydrolysis reaction is low. The 4-alkoxy-6-hydroxy-pyran-3-ones are more reactive than the corresponding 4-halo-compounds towards secondary hydrolysis to gamma-pyrones and relatively short reaction times should be employed, for example, 5 to 30 minutes at temperatures approaching 25° C., to allow suitable yields of the desired intermediate. As will be understood, the reaction time required will be a function of the temperature employed.

The formed 4-substituted-6-hydroxy-pyran-3-ones should then be separated from the acidic reaction medium to avoid hydrolysis to the corresponding gamma-pyrones. This can be effected by extraction with a suitable organic solvent such as chloroform, methylene chloride, benzene or diethyl ether. Many other organic solvents are useful for this purpose.

The 4-halo- and 4-alkoxy-6-hydroxy-pyran-3-ones prepared as described above are readily converted to gamma-pyrones by contacting with acid until conversion is substantially complete. The temperature is chosen such that the rate of the hydrolysis proceeds at a reasonable rate, preferably about 70° C. to 160° C. for the 4-halo-compounds and about 25° C. to 160° C. for the 4-alkoxy-compounds. The term "contacting with acid" used in the specification and claims hereof is intended to include both acid added to the reaction mixture and acid generated in situ by heating, both effecting the desired conversion to the corresponding gamma-pyrones.

Useful gamma-pyrones can also be prepared from novel readily prepared derivatives of 3-substituted-furfuryl alcohols of the formula

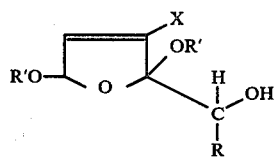

wherein R is hydrogen, alkyl of 1 to 4 carbon atoms, phenyl or benzyl, R' is alkyl of 1 to 4 carbon atoms and X is chloride, bromide, iodide or alkoxy of 1 to 4 carbon atoms. These compounds are easily prepared from the 3-substituted-furfuryl alcohols by contacting with a halogen oxidant in the presence of an alkanol of 1 to 4 carbon atoms. While this reaction is known for unsubstituted furfuryl alcohols, Achmatowitcz et al. Tetrahedron, 27, 1973 (1971); 32; 1051 (1976), the 3-substituted-2,5-dialkoxy-furfuryl alcohols are novel. the 3-halo- or 3-alkoxy-2,5-dialkoxy-furfuryl alcohols can also be prepared from compounds of the formula

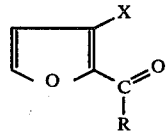

wherein R is hydrogen, alkyl of 1 to 4 carbon atoms, phenyl or benzyl and X is chloride, bromide, iodide or alkoxyl of 1 to 4 carbon atoms. After reacting with halogen in alcohol (R'OH) solution to give the 2,5-dialkoxy-analogue, the carbonyl group is converted to hydroxyl by means known in the art, such as reduction with sodium borohydride. For the preparation of maltol, isomaltol is a convenient starting material for this process.

The 3-halo- or 3-alkoxy-2,5-dialkoxy-furfuryl alcohols can be readily converted directly to the corresponding gamma-pyrones according to the reaction:

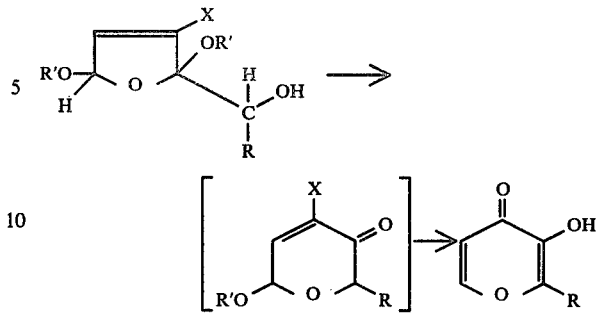

wherein R, R' and X are as previously described. To effect the conversion directly to the gamma-pyrones the 3-substituted-2,5-dialkoxy-furfuryl alcohol is contacted with acid in either aqueous or non-aqueous solution. The solution is maintained at a temperature such that the rate of conversion to the desired gamma-pyrone proceeds at a reasonable rate. Thus, the 3-halo-compounds are heated to between about 70° C. and 160° C., preferably 90° C. to 110° C., the reaction time for substantially complete conversion being about 1 to 3 hours. The 3-alkoxy-compounds are more reactive and can be converted at a reasonable rate at lower temperatures, from about 25° C. to 160° C., but preferably from 90° C. to 110° C.

The acid used to effect this conversion to the desired gamma-pyrone can be either an inorganic or organic acid with a $pK_a$ of about 5 or below. Suitable acids which are readily available include, but are not limited to, hydrochloric acid, hydrobromic acid, sulfuric acid, formic acid and p-toluene sulfonic acid. Acidic ion-exchange resins are also useful in this reaction.

The above described process can be adapted to prepare the intermediate compounds of the formula

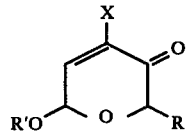

wherein R, R' and X are as previously described, by contacting the 3-halo- or 3-alkoxy-2,5-dialkoxy-furfuryl alcohol with an acid under conditions where substantially no secondary reaction to the corresponding gamma-pyrone occurs. Thus, the 3-halo- or 3-alkoxy-2,5-dialkoxy-furfuryl alcohol is contacted in non-aqueous solution with an acid at a temperature between about −50° C. and 25° C., preferably −10° C. to 10° C. The reaction can suitably be conducted in an alkanol of 1 to 4 carbon atoms, preferably methanol, but other non-aqueous solvents may be used. The 3-alkoxy-compounds are more reactive than the 3-halo-compounds and shorter reaction times are employed to obtain suitable yields of the desired intermediate while minimizing secondary reaction to the corresponding gamma-pyrone. For example, at temperatures approaching 25° C., reaction times as short as 5 minutes may be appropriate. The reaction time employed will, of course, vary with the temperature of the reaction and the strength of the acid employed. The desired 4-substituted-6-alkoxy-pyran-3-ones should then be separated from the acidic reaction medium to avoid hydrolysis to the corresponding gamma-pyrone. This can be effected by extraction with a suitable organic solvent such as chloroform, methylene chloride, benzene or diethyl ether. Many other organic solvents may be used for this purpose.

The 4-halo- or 4-alkoxy-intermediate prepared as described above can be readily converted to the corresponding gamma-pyrone by heating in the presence of an acid until conversion is substantially complete. The solution is maintained at a temperature such that the rate of conversion proceeds at a reasonable rate. For the 4-halo-compounds, a temperature of about 70° C. to 160° C. is employed, generally 90° C. to 110° C., the reaction then being substantially complete in 1 to 3 hours. The 4-alkoxyl-compounds are more reactive and temperatures in the range of about 25° C. to 160° C., preferably 90° C. to 110° C. can be employed, reaction times being shorter than for 3-halo-compounds depending on the temperature.

The present invention is illustrated by the following examples. It should be understood, however, that the invention is not limited to the specific details of these examples.

EXAMPLE 1

Isomaltol-O-methyl ether can be prepared by the method of J. E. Hodge and E. C. Nelson, Cerial Chemistry, 38, 207 (1961). A more convenient procedure is as follows: To a well stirred solution of isomaltol (56.0 g, 0.50 moles) in 300 ml of 10% KOH solution was added 63 g (0.5 moles) of dimethyl sulfate. The temperature during the addition was maintained at 25° C. The reaction was then cooled to 0°. The solid that formed was filtered and washed with ice cold water to yield 17.8 g of first crop product. The aqueous filtrate was extracted with chloroform and the chloroform concentrated to yield 7.2 g of additional product, m.p. 103°–104° C.

Isomaltol-O-methyl ether (4.04 g, 0.029 moles) in 100 ml methanol was cooled to 0° and NaBH$_4$ (2.2 g, 0.058 moles) added slowly in several portions. Extraction of the product with chloroform and concentration afforded 2.0 g of crude 2-(1-hydroxyethyl)-3-methoxy furan, NMR (CDCl$_3$+D$_2$O, δ) 7.02 (1H, d, J=2Hz), 6.18 (1H, d, J=2Hz), 4.30 (1H, q, J=7Hz), 3.62 (3H, s).

2-(1-hydroxyethyl)-3-methoxy-furan (0.350 g, 2.5 mmole) in 4 ml of methanol and 1 ml of water was added to a solution of 2 ml of methanol and 5 ml of water as chlorine gas (2.5 mmoles) was added to the well stirred reaction. The temperature of the reaction was kept below −10° C. at all times. Following the addition the reaction was heated to 90° C. for 3 hours. After cooling, the reaction was adjusted to a pH 2.2 with 50% NaOH solution, the reaction was extracted with chloroform and the chloroform concentrated to yield maltol.

EXAMPLE 2

2(1-hydroxyethyl)-3-methoxy-furan may be converted to maltol by repeating the one-pot method employing the conditions of Example 1 but replacing the chlorine oxidant with one equivalent of each of the following oxidants: bromine, chlorine-bromine, hypochlorous acid, hypobromous acid, peracetic acid, m-chloroperbenzoic acid and hydrogen peroxide.

EXAMPLE 3

Gamma-pyrones may be formed from compounds of the formula

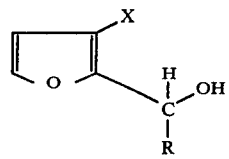

wherein R=hydrogen, methyl, ethyl, n-propyl, iso-propyl, n-butyl, phenyl or benzyl and X is methoxyl, ethoxyl, propoxyl or butoxyl, by repeating the one-pot process described in Example 1 by contacting the 3-substituted furfuryl alcohol with at least one equivalent of chlorine oxidant, or by use of the other oxidants described in Example 2.

EXAMPLE 4

2-Acetyl-3-bromofuran (1.6 g, 8.5 mmoles), made by the method of YA. L. Goldfarb, M. A. Marakathina and L. I. Belen'kii, Chem. of Heterocyclic Compounds, USSR, 6, 132 (1970) was dissolved in 15 ml of ethanol and NaHB$_4$ (0.096 g, 26 mmoles) added at room temperature. After stirring for 1.5 hours, 3-bromo-2-(1-hydroxy-ethyl)-furan (1.60 g) was isolated as a yellow oil that was purified by chromatography with silica gel to yield 0.94 g (58%) of the pure product, NMR (CDCl$_3$, δ) 7.33 (1H, d, J=2Hz), 6.4 (1H, d, J=2Hz), 5.13 (1H, q), 2.33 (1H, d), 1.57 (3H, d, J=7Hz).

To a sample of 2-(1-hydroxyethyl)-3-bromo-furan (0.54 g, 2.8 mmoles) in 15 ml water and 15 ml methanol at 0° C. was added 0.24 g (3.0 mmoles) of bromine. After allowing the reaction to come to room temperature, the reaction was treated with 3 ml of conc. HCl and heated to 96° C. for 2 hours, removing much of the methanol. After cooling, maltol was isolated by the method of Example 1.

EXAMPLE 5

Isomaltol (6.3 g, 0.05 moles) in 60 ml of CH$_2$Cl$_2$ was added dropwise over 10 minutes to a solution of PCl$_5$ (10.4 g, 0.05 moles) in 125 ml of CH$_2$Cl$_2$ at 4° C. After stirring at 4°-5° C. for 1 hour, the reaction was allowed to come to room temperature, poured into 350 ml of water and the CH$_2$Cl$_2$ layer separated. The aqueous layer was then extracted with CH$_2$Cl$_2$, the CH$_2$Cl$_2$ layers combined and then concentrated to yield a dark oil, 7.0 g. Pure 2-acetyl-3-chloro-furan was obtained by chromatography from silica gel, NMR (CDCl$_3$, δ) 7.5 (1H, d, J=2Hz), 6.56 (1H, d, J=2Hz), 2.53 (3H, s).

Anal. Calc. for C$_6$H$_5$O$_2$Cl: C, 49.85; H, 3.49. Found: C, 49.50; H, 3.46.

2-Acetyl-3-chloro-furan (1.0 g, 7 mmoles) in 30 ml methanol was cooled to 10° C. and 0.065 g, (1.7 mmoles) of NaBH$_4$ added in one portion. After stirring for 30 minutes at 25° C., the solution was treated with 15 ml of water and cooled to 5° C. To the formed 2-(1-hydroxyethyl)-3-chloro-furan was then added 1.1 g (7 mmoles) of bromine, dropwise and with cooling. After the addition was complete the reaction was heated to 95° C. for 2 hours, distilling off a portion of the methanol. The reaction was then cooled and maltol isolated by the method of Example 1.

EXAMPLE 6

2-(1-hydroxyethyl)-3-chloro-furan may be converted to maltol by repeating the method of Example 5 but replacing the methanol co-solvent with each of the following co-solvents: tetrahydrofuran, acetone, isopropyl ether, ethyl acetate, ethanol, n-propanol, dioxane, diethyl ether and ethylene glycol.

EXAMPLE 7

2(1-hydroxyethyl)-3-methoxy-furan prepared as in Example 1 may be converted to the intermediate 2-methyl-4-methoxy-6-hydroxy-2H-pyran(6H)-3-one by omitting the final heating and hydrolysis. To an aqueous methanol solution of 2(1-hydroxyethyl)-3-methoxy furan is added one equivalent of chlorine gas while stirring the solution at −10° C. The formed 2-methyl-4-methoxy-6-hydroxy-2H-pyran(6H)-3-one is isolated by extraction with chloroform and concentration.

EXAMPLE 8

The 2-methyl-4-methoxy-6-hydroxy-2H-pyran(6H)-3-one formed by the method of Example 7 may be converted to maltol by heating in 2N HCl acid solution at 90° C. for 3 hours. Maltol is isolated by extraction with chloroform and concentration.

EXAMPLE 9

To a solution of isomaltol-O-methyl ether (10.0 g, 0.072 moles), prepared as in Example 1, in 70 ml methanol was added 17.0 g (0.16 moles) of NaHCO3 and the mixture cooled to −30° C. To this well stirred solution was added a solution of 12.8 g (0.08 moles) of bromine in 10 ml methanol. The temperature of the reaction was maintained between −30° C. and 0° with cooling. After the addition period the reaction was allowed to warm to room temperature and stirred for 2 hours. The reaction was then filtered and concentrated to yield 13.4 g of a yellow oil, which was distilled at 79°–83° C./0.75 torr to yield 10.09 g (75%) of 2-acetyl-2,3,5-trimethoxy-2,5-dihydrofuran, NMR (CDCl3,δ) 5.6 (1H, d, J=2Hz), 5.1 (1H, d, J=2Hz), 3.7 (3H, s), 3.5 (3H, s), 3.37 (3H, s), 2.3 (3H, s). Chlorine can be used to replace bromine in this preparation with no significant effect on the yield of product.

2-acetyl-2,3,5-trimethoxy-2,5-dihydrofuran (9.22 g, 0.049 moles) was dissolved in 100 ml of methanol and cooled to 0° C. Solid NaBH4 (4.0 g, 0.105 moles) was added portion-wise over 1 hour, maintaining a temperature below 15° C. The reaction was then allowed to warm to room temperature, and 20 ml of saturated aqueous NH4Cl added. Extraction of the crude product with chloroform and concentration yielded 9.3 g of 2-(1-hydroxyethyl)-2,3,5-trimethoxy-2,5-dihydrofuran (100%) as a clear 0.1, NMR (CDCl3+D2O,δ) 5.5 (1H, m), 5.03 (1H, M), 3.8 (4H, m), 3.58 (3H, s), 3.3 (3H, s), 1.10 (3H, t). 2(1-hydroxy ethyl)-2,3,5-trimethoxy-2,5-dihydrofuran (2.82 g, 0.015 moles) in 2 ml methanol was added to 15 ml of formic acid over 5 minutes. To the well stirred solution was then added 20 ml of water and the reaction heated to reflux for 1 hour. After cooling, the reaction was extracted with chloroform and the chloroform concentrated to yield 1.5 g maltol, which was recrystallized from methanol to yield the pure white solid, m.p. 159°–160° C. Hydrochloric acid, hydrobromic acid, p-toluene sulfonic acid and acidic ion exchange resins can be used in place of formic acid in this Example.

EXAMPLE 10

2(1-hydroxy ethyl)-2,3,5-trimethoxy-2,5-dihydrofuran (2.30 g, 0.012 moles) was stirred at room temperature for 4 hours in 50 ml of 1N H2SO4. Isolation as described in Example 9 gave 67% assayed yield of pure maltol.

EXAMPLE 11

2(1-hydroxy ethyl)-2,3,5-trimethoxy-2,5-dihydrofuran (8.4 g, 0.45 moles) in 3 ml methanol was added to 25 ml of formic acid and 1.2 ml methanol. After stirring for 5 minutes, the reaction was poured into 75 ml of water and extracted with chloroform. Concentration of the chloroform layer yielded a brown oil which solidified overnight. Recrystallization from hexane-ether yielded 4,6-dimethoxy-2-methyl-2H-pyran-3(6H)-one as white needles, mp 73°–74.5° C., NMR (CDCl3,δ) 5.75 (1H, d, J=4Hz), 5.3 (1H, d, J=4Hz), 4.62 (1H, q, J=7Hz), 3.68 (3H, s), 3.52 (3H, S), 1.2 (3H, t, J=7Hz).

EXAMPLE 12

4,6-dimethoxy-2-methyl-2H-pyran-3(6H)-one (0.65 g, 3.8 mmoles) was added to 10 ml of 2M H2SO4 solution. After 40 minutes the pH of the reaction was adjusted to 2.2 with 6N NaOH and maltol (74%) isolated as described in Example 9.

EXAMPLE 13

2-(1-hydroxy ethyl)-3-bromo-2,5-dimethoxy-furan may be prepared by reacting a methanol solution of 2(1-hydroxy ethyl)-3-bromo-furan, prepared as shown in Example 4, with one equivalent of bromine while stirring the solution at −10° C. The desired compound is isolated by chloroform extraction and concentration.

The 2-(1-hydroxy ethyl)-3-bromo-2,5-dimethoxy-furan may be converted to maltol by addition of a methanol solution of this compound to formic acid and heating to reflux for one hour. Maltol is isolated by chloroform extraction and concentration.

EXAMPLE 14

2-methyl-4-bromo-6-methoxy-2H-pyran(6H)-3-one may be prepared by addition of a methanol solution of 2(1-hydroxy ethyl)-3-bromo-2,5-dimethoxy-furan to formic acid at a temperature of 0° C. After about one hour, the desired 2-methyl-4-bromo-6-methoxy-2H-pyran(6H)-3-one is isolated by chloroform extraction and concentration.

EXAMPLE 15

2-methyl-4-bromo-6-methoxy-2H-pyran(6H)-3-one prepared as in Example 14 may be converted to maltol by adding a methanol solution of the compound to 2N sulfuric acid and refluxing for 2 hours. Maltol is isolated by chloroform extraction and concentration.

EXAMPLE 16

The method of Example 13 may be repeated employing as starting materials furfuryl alcohols of the formula

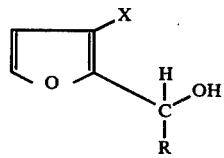

wherein R is hydrogen, methyl, ethyl, propyl, butyl, phenyl and benzyl and X is chloride, bromide, iodide, methoxyl, ethoxyl, propoxyl and butoxyl. The furfuryl alcohols are contacted with bromine oxidant in the presence of methanol, ethanol, propanol or butanol at −10° C. and thereafter the solutions are heated to 90° C. in the presence of formic acid to yield the desired gamma-pyrones.

What is claimed is:

1. A process for preparing a gamma-pyrone of the formula

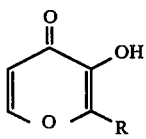

which comprises contacting a compound of the formula

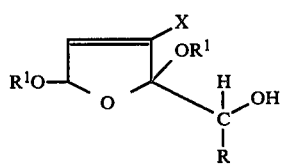

wherein R is hydrogen, alkyl of 1 to 4 carbons, phenyl or benzyl; $R^1$ is alkyl of 1 to 4 carbons; and X is chloro, bromo, iodo or alkoxyl of 1 to 4 carbons, with an acid having a pKa of about 5 or below until conversion to the desired gamma-pyrone is substantially complete.

2. The process of claim 1 wherein the contacting is conducted at between about 70° C. and 160° C.

3. The process of claim 1 where the compound of the formula

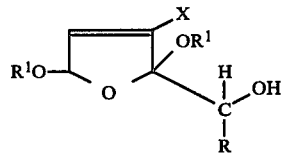

is prepared by contacting a compound of the formula

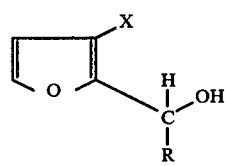

with a halogen oxidant in the presence of a compound of the formula $R^1OH$.

4. The process of claim 1 wherein the compound of the formula

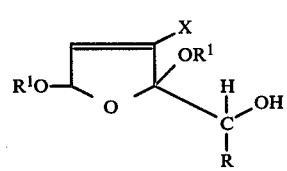

is prepared by (a) contacting a compound of the formula

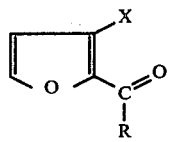

with a halogen oxidant in the presence of a compound of the formula $R^1OH$ to form a compound of the formula

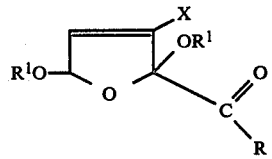

and (b) contacting the compound formed in step (a) with a reducing agent effective to convert the carbonyl group to hydroxyl.

5. The process of claim 1 wherein the acid is selected from hydrochloric acid, hydrobromic acid, sulfuric acid, formic acid, p-toluene sulfonic acid and acidic ion exchange resins.

6. The process of claim 1 wherein said gamma-pyrone is 2-methyl-3-hydroxy-4H-pyran-4-one.

7. The process of claim 1 wherein said gamma-pyrone is 2-ethyl-3-hydroxy-4H-pyran-4-one.

8. A process for preparing a compound of the formula

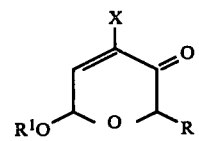

which comprises contacting a 3-substituted-2,5-dialkoxy-furfuryl alcohol of the formula

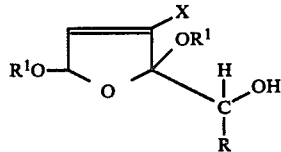

wherein R is hydrogen, alkyl of 1 to 4 carbon atoms, phenyl or benzyl; $R^1$ is alkyl of 1 to 4 carbon atoms; and X is chloride, bromide, iodide or alkoxyl of 1 to 4 carbon atoms, with acid in non-aqueous solution at a temperature between −50° C. and about 25° C. and separating said compound before substantial hydrolysis occurs.

9. A process for preparing a gamma-pyrone of the formula

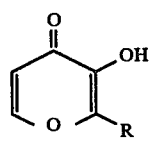

which comprises contacting a compound of the formula

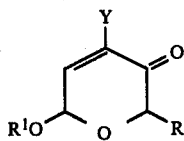
wherein R is hydrogen, alkyl of 1 to 4 carbon atoms, phenyl or benzyl; $R^1$ is hydrogen or alkyl of 1 to 4 carbon atoms; and Y is alkoxyl of 1 to 4 carbon atoms, with acid until conversion to the desired gamma-pyrone is substantially complete.
10. The process of claim 9 wherein the contacting is conducted at a temperature between 25° C. and 160° C.
* * * * *